(12) United States Patent
Guan

(10) Patent No.: US 6,228,587 B1
(45) Date of Patent: May 8, 2001

(54) CHROMOSOME MICRODISSECTION METHOD

(76) Inventor: Xin-Yuan Guan, 5111 Parklawn Terrace, Apt. 204, Rockville, MD (US)

( * ) Notice: Subject to any disclaimer, the term of this patent is extended or adjusted under 35 U.S.C. 154(b) by 0 days.

(21) Appl. No.: 09/264,028

(22) Filed: Mar. 8, 1999

(51) Int. Cl.⁷ .............................. C12Q 1/68; C12P 19/34
(52) U.S. Cl. ................................ 435/6; 435/91.2
(58) Field of Search ..................... 435/6, 91.2; 536/23.1

(56) References Cited

U.S. PATENT DOCUMENTS 5,545,524 * 8/1996 Trent et al. ................................ 435/6

OTHER PUBLICATIONS

Alberts et al., The Molecular Biology of the The Cell. 2nd ed. Garland Publishing, Inc. New York, 1989.*

Nenno et al., Genome, vol. 37, pp 1018–121, 1989.*

* cited by examiner

Primary Examiner—W. Gary Jones
Assistant Examiner—Jehanne Souaya
(74) Attorney, Agent, or Firm—Greenberg Traurig LLP

(57) ABSTRACT

A method for improving the amplification of microdissected DNA fragments includes treating the fragments with pepsin prior to amplification.

7 Claims, No Drawings

CHROMOSOME MICRODISSECTION METHOD

FIELD OF THE INVENTION

The present invention relates generally to the microscopic dissection of chromosomes into specific regions that are then subjected to study. More specifically, it relates to the amplification of such microdissected chromosome regions so that such study may be more readily and intensely conducted.

BACKGROUND OF THE INVENTION

Chromosome microdissection is a recently developed molecular cytogenetic technique which has become increasingly important as a bridge connecting cytogenetics to molecular genetics. After a decade of effort, this approach has been developed into a useful and reproducible approach for several purposes, including: 1) the isolation of DNA from any cytogenetically recognizable region which can be used to generate DNA microclone libraries for molecular analysis and positional cloning; (see Guan, X -Y, Meltzer P. S., Cao, J. and Trent, J. M.: Rapid generation of region-specific genomic clones by chromosome microdissection: Isolation of DNA from a region frequently deleted in malignant melanoma. *Genomics* 14: 680–684, 1992; and Leach, F. S., Nicolaides, N. C., Papadopoulos, N., Liu, B., Jen, J. Parsons, R., Peltomaki, P., Sistonen, P. Aaltonen, L. A., Nystrom-Lahti, M., Guan, X -Y, Zhang, J., Meltzer, P. S., Yu, J -W, Kao, F -T, Chen, D. J., Cerosaletti, K. M., Fournier, R. E. K., Todd, S., Lewis, T., Leach, R. J., Naylor, S. L., Weissenbach, J., Mecklin, J -P, Jarvinen, H., Petersen, G. M., Hamilton, S. R., Green, J., Jass, J., Watson, P., Lynch, H. T., Trent, J. M., de la Chapell, A., Kinzler, K. W., and Vogelstein, B.: Mutations of a mutS homolog in hereditary nonpolyposis colorectal cancer. *Cell* 75: 1215–1225, 1993); 2) the generation of fluorescent in situ hybridization (FISH) probes for whole chromosome painting probes (see Guan, X -Y, Meltzer, P. S. and Trent, J. M.: Rapid construction of whole chromosome painting probes by chromosome microdissection. *Genomics* and 22: 101–107, 1994) and chromosome arm painting probes (Guan, X -Y, Zhang, H. E., Bitter, M., Jiang, Y., Meltzer, P. ., and Trent, J. .: Chromosome arm painting probes. Nature *Genet* 12: 10–1996) for cytogenetic study; 3) combined with fluorescent in situ hybridization, microdissection has been applied to virtually detect virtually any kind of visible chromosome rearrangements (Guan, X -Y, Meltzer, P. S., Bittner, M., Trent, J. M.: Identification of cryptic sites of DNA sequence amplification in human breast cancer by chromosome microdissection. *Nature Genet* 8: 155–161, 1994; and Guan, X -Y, Zhang, H. E., Horsman, D., Meltzer, P. S. and Trent, J. M.: Mapping a recurrent breakpoint on chromosome 6q11 in human follicular lymphoma by chromosome microdissection. *Blood* 88: 1418–1422, 1996). More recently, 4) microdissection combined with hybrid selection has been applied to identify genes associated with homogeneously staining regions (HSR's) in human cancers (Su, Y. A., Meltzer, P. S., Guan, X -Y, and Trent, J. M.: Direct isolation of expressed sequences encoded within a homogeneous staining region by chromosome microdissection. *Proc Nat Aca Sci USA* 91: 9121–9125, 1994; and Guan, X -Y, Xu, J., Anzick, S. L., Zhang, H. E., Trent, J. M., and Meltzer, P. S.: Direct selection of transcribed sequences from microdissected DNA: Isolation of genes within a commonly amplified region at 20q1-q13.2 in breast cancer. *Cancer Res* 56: 3446–3450, 1996.)

The process of chromosome microdissection technique includes two parts, microdissection of a target chromosomal region under a microscope using a finely drawn glass needle and subsequent amplification of the dissected DNA fragments with a degenerate oligonucleotide primer by polymerase chain reaction (PCR). Briefly, 5–10 copies of target chromosmeal region are microdissected with glass needle and transferred to a PCR tube containing collection solution. Microdissected DNA fragments are then amplified by PCR. FISH with labeled microdissected PCR products is then routinely used in this protocol to evaluate the experimental result.

While the basic steps of microdissection, amplification and labeling the amplified DNA fragment is known to the art, it has also been recognized that certain microdissection techniques require large amounts of time to accomplish and are highly labor intensive. Thus, dissecting 20 or 30 DNA from a target region to obtain a sufficient template for PCR amplification is an onerous task, and repeated use of a microdissection needle increases the possibility of DNA contamination. As a consequence, it has been a desire of those in this art to provide a method of generating whereby amplification of microdissected chromosome fragments can be accomplished with greater ease and effectiveness, so that the number of microdissected fragments subjected to amplification is substantially decreased, thereby simultaneously decreasing the time spent in accomplishing the dissection as well as the possibility of contamination.

Indeed, the problem is addressed in U.S. Pat. No. 5,545,524 to Trent et al., which discloses a procedure in which a dissected DNA fragment is treated with topoisomerase I prior to amplification of the fragment. Although these patentees state that it is difficult to model the precise effect of Topo I on dissected DNA fragments, it is theorized highly coiled DNA impairs access of primer and DNA polymerase to the template, and that the use of Topo I promotes relaxation of the template DNA, thus permitting access to be more readily effected. Where access is more easily effected, amplification is more readily and easily accomplished.

SUMMARY OF THE INVENTION

The present invention is directed to greatly improving amplification of microdissected DNA fragments by treating the fragments with pepsin prior to amplification. In this manner the efficacy of the amplification is greatly improved, thereby reducing the number of DNA fragments required to later generate probes. In this manner the risks of contamination and time for microdissection to be effected are substantially reduced.

DETAILED DESCRIPTION OF A PREFERRED EMBODIMENT

A preferred protocol for the preparation of a FISH probe, beginning with the formation of metaphase chromosome from a blood sample, microdissection of the target chromosome, pepsin treatment of the dissected DNA fragments, amplification of the dissected fragments by polymerase chain reaction techniques, and, finally, the preparation of a FISH probe from the amplified fragments, is set forth hereinafter. However, it will be apparent that this detailed protocol may be varied by those of skill in the art, and that the protocol is that which is preferred by the inventor at the present time.

Preparation of Metaphase Chromosome

1. Add 0.5 ml peripheral blood to 4.5 ml Complete RPMI 1640 medium and culture for 64–68 hours at 37° C.

2. Add 25 µl colcemid (10 µg/ml) to the culture medium and incubate at 37° C. for 20 minutes.

3. Transfer the cells to a 15 ml centrifuge tube and centrifuge at 250×g for 5 minutes and then carefully discard the supernatant.

4. Resuspend and incubate the remaining cell pellet in 10 ml of hypotonic solution (0.075 M KCl) in a 37° C. waterbath for 18 minutes. Centrifuge at 250×g for 5 minutes and then remove the supernatant, leaving 0.2–0.5 ml to resuspend cell pellet.

5. Resuspend the remaining cell pellet thoroughly but gently in 8 ml freshly prepared Carnoy's fixative (3:1 methanol and glacial acetic acid) and place on ice for a minimum of 2 hours. Centrifuge at 250×g for 5 minutes and then remove the supernatant carefully.

6. Wash the cells twice with 5 ml Carnoy's fixative by centrifuging at 250×g for 5 minutes.

7. Resuspend the cell pellet in 0.5–1.5 ml Carnoy's fixative to obtain a lightly opaque cell suspension before preparing slides.

8. Drop 2–3 drops of cell suspension onto a clean coverslip (22×60 mm) held at 45° angle, allowing the cell suspension to run down the length of the coverslip. Do not blow on the slide to avoid contamination.

9. Keep the prepared coverslips in a sterile container at room temperature for 3–10 days prior to banding.

10. Standard G-banding with trypsin-Giemsa (GTG) is performed prior to microdissection. Briefly, treat the slide with trypsin working solution at room temperature for 1–2 minutes. Transfer the slide to Giemsa working solution for 6 minutes at room temperature, then rinse the slide with distilled water and air dry.

All steps above should be performed under sterile conditions.

Microdissection and Pepsin Treatment

1. Find the target chromosome under an inverted microscope fitted with a stage which can be freely rotated to allow positioning of any chromosome perpendicular to the axis along which the glass needle is moved. If possible, the microscope should reside on a massive stand to dampen vibration.

2. Dissect the target chromosomal region with glass needles controlled by a hydraulic micromanipulator (Narishige, Japan) attached to the inverted microscope.

3. Pick up the dissected DNA fragment with the needle by positioning the tip of the needle directly above the DNA fragment and then moving the needle down and lightly touching the fragment. The DNA fragment will be held to the tip by electrostatic forces and then is transferred into a 5 µl collection solution [100 mM tris-HCl, pH 8.4, 20 mM $MgCl_2$, 500 mM KCl, 0.1 mg/ml gelatin, 200 µM each of dNTP, 2 µM UN1 primer (5'CCGACTCGAGNNNNNNATGTGG), 0.5 mg/ml pepsin] by touching the needle tip to the fluid.

4. After the desired number of dissected DNA fragments (5–10 copies) are collected, the collection solution is covered with a drop of mineral oil. Before the amplification of microdissected DNA, the DNA has been treated with pepsin in the collection solution to remove proteins tightly binding to the DNA and permit the very tight DNA coiling to loosen. Incubate the collection solution containing dissected DNA fragments at 45° C. for 1 hour, and then terminate the reaction by heating to 96° C. for 10 minutes.

Amplification of Dissected DNA

1. An initial 5–8 cycles of PCR (denaturation at 94° C. for 1 minute, annealing at 30° C. for 2 minutes, and extension at 37° C. for 2 minutes) are conducted by adding approximately 0.3 units of Sequenase (US Biochemicals, Cleveland, Ohio) at 30° C. each cycle [Sequenase (13 units/µl) is diluted 1 to 8 in enzyme dilution buffer (US Biochemicals), and 0.2 µl is added to the 5 µl reaction mixture].

2. Following this pre-amplification step, a conventional PCR reaction catalyzed by Taq DNA polymerase is performed in the same tube. 50 µl PCR reaction mixture [100 mM Tris-HCl, pH 8.4, 20 mM $MgCl_2$, 500 mM KCl, 0.1 mg/ml gelatin, 200 µM each of dNTP, 2 µM UN1 primer (5'-CCGACTCGAGNNNNNNATGTGG), 2 Unit Taq polymerase] is then added and the reaction is heated to 95° C. for 3 minutes followed by 30 cycles at 94° C. for 1 minute, 1 minute at 56° C., 2 minutes at 72° C., with a 5 minutes final extension at 72° C.

3. Add 2 µl of above PCR products into another 50 µl PCR reaction mixture and perform 20 PCR cycles identical to that described above.

4. The success of the process can be judged at this point by agarose gel analysis of 5 µl of the amplified PCR products. The size distribution of PCR products is in the size range of 200 to 600 base pairs.

Fluorescent In Situ Hybridization (FISH)

1. Prepare a FISH probe by the addition of 2 µl of second round PCR products into a 50 µl PCR reaction mixture identical to that described above except for the addition of 20 µM Biotin-16-dUTP (Boehringer Mannheim GmbH, Germany) for final concentration. The PCR reaction is continued for 15–20 cycles of 1 minute at 94° C., 1 minute at 56° C., and 2 minutes at 72° C., with a 5 minutes final extension at 72° C.

2. Remove the unincorporated Biotin-16-dUTP from the product by centrifuging on a Bio-gel P6 filtration column (BioRad, Hercules, Calif.) following the manufacturer's instructions. Briefly, resuspend the settled gel, snap off the tip and place the column in a 2.0 ml microcentrifuge tube, allow the excess packing buffer to drain by gravity and discard the drained buffer, centrifuge the column for 2 minutes at 1,000×g to remove the remaining packing buffer, place the column in a clean 1.5 ml microcentrifuge tube, load the sample directly in to the center of the column and centrifuge the column for 4 minutes at 1,000×g.

3. Recover the probe by precipitation with ¹/₁₀ volume of 3 M sodium acetate (pH 5.2) and 2 volumes of ethanol for 10 minutes at 4° C. and centrifugation at 10,000×g for 15 minutes at 4° C. Resuspend the probe in 40 µl TE buffer (10 mM Tris HCl, 1 mM EDTA, pH 7.5).

4. Hybridization of the FISH probes is based upon the procedure described more fully by me in Guan, X -Y et al., Generation of Band-Specific Painting Probes from a Single Microdissected Chromosome, *Human Mol. Genet.*, 2, 1117–1121 (1993), which procedure is incorporated by reference herein. For each hybridization, about 100 ng labeled probe (2 µl) is mixed in 10 µl hybridization mixture (50% formamide, 2×SSC, 10% dextran sulfate, 1 µg human Cot I DNA) which is denatured at 75° C. for 5 minutes followed by 20 minutes incubation at 37° C.

5. Denature a slide bearing metaphase spreads for 2 minutes at 70° C. in denaturing solution (70% formamide, 2×SSC), then dehydrate the slide through a series of 70%, 85%, and 100% ethanol.

6. Place the hybridization mixture on the slide previously denatured and cover with a 22×22 mm coverslip, seal with rubber cement, and incubate the slide at 37° C. overnight in a humidified container.

7. After hybridization, the coverslip is removed and the slide is processed through a series of 3 washes in 50% formamide, 2×SSC, 1 wash in 4×SSC, 0.1% NP40 (Calbiochem, La Jolla Calif.) and 1 wash at 4×SSC, all at 45° C., for 5–10 minutes each.

8. Hybridization involving only directly labeled probes can be analyzed at this point. Hybridization involving a biotin labeled probed is then treated with 40 µl FITC-conjugated avidin (5 µg/ml) (Vector Laboratories, Burlingame, Calif.) in PNM buffer for 20 minutes at room temperature. The slide is then washed 3 times in 4×SSC, 0.1% NP40 and 1 time in 4×SSC at room temperature two minutes each.

9. The fluorescence signal is then amplified by treating the slide with 40 µl anti-avidin antibody (5 µg/ml) (Vector Laboratories) in PNM buffer for 20 minutes at room temperature. The slide is then washed 3 times in 4×SSC, 0.1% NP40 and 1 time in 4×SSC at room temperature two minutes each.

10. Preferably the slide is treated with one more layer of FITC-conjugated avidin in the same manner as that described above.

11. The slide is dehydrated through a series of 70%, 85%, and 100% ethanol washes and air dried. Counterstain the slide with 40 µl antifade solution (Vector Laboratories) containing DAPI (0.5–1 µg/ml) or propidium iodide (0.5–1 µg/ml). The slide is then coverslipped and examined with an epi-fluorescence microscope equipped with appropriate filters.

In contrasting the pepsin treatment of DNA fragments prior to PCR amplification with the prior art treatment by topoisomerase I, it is first noted that pepsin is a far more economic material, being found in the gastric juice of mammals, birds, reptiles and fish. Pepsin is prepared commercially from the glandular layer of fresh hog stomachs. It is economic because of its many other uses in industrial processes that require large volumes of pepsin. For example, it is part of a crude preparation known as rennet, which is used to modify soyprotein and gelatin, thereby providing whipping qualities, to make precooked cereals into instant, hot cereals, and to prevent the formation of cloudiness in beer. Because of these and many other uses of pepsin on a large, commercial scale, its properties have become well known and its cost has declined in inverse proportion to its use. It can easily be handled and ingested; it has even been categorized by the U.S. Food and Drug Administration as "generally recognized as safe."

Not only does pepsin have economic and other advantages as contrasted with Topo I, but it is believed to be more effective in pre-treatment of DNA fragments prior to amplification by PCR. While both pepsin and topoisomerase I are enzymes, it is believed that they effect the DNA structure in different ways. Pepsin is a proteinase that digests and removes the DNA binding protein or histone (cromotin structure protein), thus making the DNA helix looser. Topo I, on the other hand, is said to relax or release the structure, thus bringing about no real change in the structure as does pepsin. Thus, on a theoretical basis as well, pepsin is superior in restructuring the DNA fragments so that they can more readily be amplified when subjected to a polymerase chain reaction.

While my invention has been described hereinbefore in terms based on a preferred embodiment thereof, it will be apparent to those of ordinary skill in the art that many alterations and modifications may be made in that preferred embodiment without departing from the scope of the invention. It is desired, therefore, that my invention include all such obvious alterations and modifications and that it be limited only by the purview, including equivalents, of the following, appended claims.

I claim:

1. A method of improving the amplification of microdissected DNA fragments, comprising treating the fragments with pepsin, and thereafter subjecting the fragments to amplification.

2. A method as claimed in claim 1, in which the amplification includes a polymerase chain reaction.

3. A method as claimed in claim 1, in which the DNA fragments are labeled after amplification.

4. A method as claimed in claim 3, in which the label is fluorescent.

5. A method of preparing a FISH probe comprising the steps of (a) microdissecting DNA fragments, (b) treating the fragments with pepsin, (c) amplifying the pepsin-treated fragments, and (d) thereafter subjecting the amplified fragments to a polymerase chain reaction mixture containing biotin.

6. A method as claimed in claim 5, in which the amplification step includes a polymerase chain reaction.

7. A method of localizing a chromosomal region of interest in a chromosome sample having nucleic acid sequences, comprising:

(a) generating a chromosome region-specific probe by
  (i) microdissecting the chromosomal region of interest to form a DNA fragment,
  (ii) treating the DNA fragment with pepsin,
  (iii) subjecting the treated fragment to amplification, and
  (iv) labeling the amplified fragment to provide the probe;

(b) contacting the chromosome sample with the probe under conditions favorable for hybridization between the probe and complementary nucleic acid sequences in the sample, and (c) determining the existence and location of hybridization in the chromosome sample.

* * * * *